United States Patent [19]

Bruckner et al.

[11] Patent Number: 4,971,999

[45] Date of Patent: * Nov. 20, 1990

[54] ODORLESS AROMATIC DIALDEHYDE DISINFECTING AND STERILIZING COMPOSITION AND METHOD OF USING THE SAME

[75] Inventors: Norman I. Bruckner, Plano; Michael D. Gordon; Ronald G. Howell, both of Arlington, all of Tex.

[73] Assignee: Johnson & Johnson Medical, Inc., Arlington, Tex.

[*] Notice: The portion of the term of this patent subsequent to Jul. 25, 2006 has been disclaimed.

[21] Appl. No.: 349,675

[22] Filed: May 10, 1989

Related U.S. Application Data

[63] Continuation-in-part of Ser. No. 53,208, May 21, 1987, Pat. No. 4,851,449.

[51] Int. Cl.$^5$ ............................................. A61K 31/11
[52] U.S. Cl. .................................................... 514/698
[58] Field of Search ......................................... 514/698

[56] References Cited

U.S. PATENT DOCUMENTS

| | | | |
|---|---|---|---|
| 3,912,450 | 10/1975 | Boucher | 514/705 |
| 3,968,248 | 7/1978 | Boucher | 514/705 |
| 3,968,250 | 7/1978 | Boucher | 514/705 |
| 4,436,754 | 3/1984 | Jacobs | 514/694 |
| 4,851,449 | 7/1989 | Bruckner et al. | 514/698 |

OTHER PUBLICATIONS

Rehn et al., Z61, Bakt Hyg. B172, 508–19, 1981.
Rehn et al., Z61, Bakt. Hyg. B168, 507–16 (1979).

*Primary Examiner*—Mukund J. Shah
*Assistant Examiner*—E. C. Ward

[57] ABSTRACT

An odorless sterilizing and disinfecting solution is described which has a pH of from 3 to 9 and which contains an effective amount of phthalaldehyde. The solution is used to sterilize or to disinfect a surface in need of such treatment.

8 Claims, No Drawings

1

ODORLESS AROMATIC DIALDEHYDE DISINFECTING AND STERILIZING COMPOSITION AND METHOD OF USING THE SAME

This application is a continuation-in-part of application Ser. No. 53,208, filed on May 21, 1987 now U.S. Pat. No. 4,851,449.

FIELD OF INVENTION

This invention relates to stable, odorless sterilizing and high level disinfecting compositions which contain a water soluble aromatic dialdehyde as the active ingredient, and to the use of such compositions to disinfect or to sterilize a surface in need of such treatment. The dialdehyde employed is 1,2-benzenedicarboxaldehyde, commonly referred to as o-phthalaldehyde or phthalaldehyde.

PRIOR ART

Saturated dialdehyde sterilizing and disinfecting compositions are known and are widely used in commerce. Pepper et al., U.S. Pat. No. 3,016,328; to Stonehill, U.S. Pat. No. 3,282,775; Boucher, U.S. Pat. Nos. 3,708,263, 3,912,450, 3,968,248 and 3,968,250; and Buchalter, U.S. Pat. No. 3,983,252 all disclose the use of glutaraldehyde in aqueous or alcoholic solutions used to disinfect or sterilize medical devices or environmental surfaces.

Jacobs, U.S. Pat. No. 4,436,754 discloses low odor glutaraldehyde sterilizing and disinfection compositions.

Rehn and Nolte in *Zentralblatt fuer Bakteralogie, Parasitenkunde, Infektionskrankheitec und Hygiene.*, 1 Abt. Orig. B 168, pp. 507–516 (1979) disclose that a range of aromatic monoaldehydes and one aromatic dialdehyde, terephthalaldehyde, have bacteriostatic and fungistatic activity.

Rehn, Nolte, and Zerling in *Zentralblatt fuer Bakteralogie, Parasitenkunde, Infektionskrankheitec und Hygiene.* 1 Abt. Orig. B 172, pp 508–519 (1981) disclose that phthalaldehyde, isophthalaldehyde and terephthalaldehyde all have bacteriostatic and fungistatic activity.

Commercially available high level disinfecting glutaraldehyde compositions of the type disclosed in the above mentioned U.S. Patents have long been considered to be effective against a broad range of microorganisms, including *Mycobacterium tuberculosis* in ten (10) minutes at a temperature of 20° C. The test employed to make the determination of effectiveness was the AOAC Tuberculocidal Test, as specified in *Official Methods of Analysis* of the Association of Official Analytical Chemists, 14th Edition, 1984, Sections 4.045–4.050. In this Test, the organism employed is *Mycobacterium bovis* BCG.

It is now apparent that the standard AOAC test method gives highly erratic and variable results. This test method can show that a disinfectant composition is effective against *Mycobacterium bovis* BCG in 10 minutes, when in fact it is much less effective than the test indicated. An improved test method, which is both reproducible and quantitative, has been developed. The new test method uses the same test organism as the above mentioned AOAC Tuberculocidal Test. In this new test method, nine milliliters (ml) of the germicide to be tested is placed in a tube, put into a water bath and allowed to come to the desired temperature. One ml of the test organism (*M. bovis* BCG) is added to the tube containing the germicide to be tested. At appropriate time intervals, aliquots of the germicide-cell suspension are removed and added directly to an equal volume of appropriate neutralizer and mixed thoroughly. Ten-fold dilutions of the neutralized sample are prepared with saline dilution blanks. One ml of the appropriate dilutions are collected on the surface of membrane filters having a pore size of 0.45 micrometer. The filters are then washed with at least 50 ml of saline. The filters are placed on agar plates and incubated in plastic bags for 15 to 20 days at 37° C. The surviving colonies are then counted. Survival curves are constructed to determine the tuberculocidal activity of the solution. The data is plotted as $S/S_o$ vs. time. $S_o$ is the initial viable count of the test organism culture and S is the viable count at each time point.

When commercial glutaraldehyde solutions are tested using the new quantitative test method, these compositions do not kill the required $1 \times 10^5$ *Mycobacterium bovis* BCG in 10 minutes at 20° C. The additional exposure time required for complete kill at 20° may be as much as several hours. This exposure time becomes impractical, since the desired turn-around time for disinfection of equipment, especially heat-sensitive fiberoptic endoscopes, in the hospital is 30 minutes or less. In order to achieve this equipment turn-around time, a disinfection time of 10 minutes or less is required. In order to obtain a 10 minute kill time, a temperature of 30° C. is required. Since the normal hospital room temperatures are between 20° C. and 25° C., additional costs associated with heating conventional glutaraldehyde compositions would be required to kill all the organisms within the desired 10 minute time period.

High level disinfectants are not only capable of rapid kill against Mycobacteria. but are effective against the resistant nonlipid and small viruses and with extended exposure times, capable of actual sterilization. It is well known by one skilled in the art that the degree of effectiveness of high level disinfectants is not only controlled by temperature and contact time, but is dependent on active ingredient content and the solution pH. The previously cited references about aromatic dialdehydes do not recognize that phthalaldehyde is a high level disinfectant. It has excellent activity against *Mycobacterium tuberculosis* and Poliovirus Type I. These references also do not recognize that the corresponding 1,3- and 1,4-isomers have little if any high level disinfecting activity. Compositions which contain low concentrations of phthalaldehyde (e.g., 0.25%) as the sole active ingredient are effective against the above-mentioned organisms in 10 minutes or less at a temperature of 20° C. Phthalaldehyde, at the same low concentrations, has sporicidal activity against *Bacillus subtilis* and *Clostridium sporogenes* spores in 24 hours at a temperature of 20° C. At higher concentrations (e.g., 1.0%) of phthalaldehyde, sterilization is achieved in 10 hours. The sporicidal and high level disinfecting activities of compositions with phthalaldehyde are maintained over the pH range 3 to 9.

Storage stability and ease of product use are two important considerations when selecting sterilizing and high level disinfecting solutions. Glutaraldehyde-based compositions are more effective as high level disinfecting and sterilizing solutions at alkaline pH than at neutral or acidic pH values. However, glutaraldehyde and other similar aldehydes with alpha hydrogens autopolymerize at an alkaline pH. Compositions containing these aldehydes at an alkaline pH experience a reduction in the effective concentration of the aldehyde with time and, therefore, have limited storage stability. In order to overcome this problem, the aldehyde composition must be packaged in two or more components. These aldehydes can be formulated in an aqueous solution at an acid pH, and activated with an alkalinating agent immediately prior to use, shifting the pH to the alkaline range. This procedure is disclosed in the previously mentioned Pepper et al. patent, U.S. Pat. No. 3,016,328. Unlike the aforementioned aldehydes, phthalaldehyde does not have alpha hydrogens and therefore cannot undergo autopolymerization at an alkaline PH. Compositions containing phthalaldehyde can be formulated as a single component. These compositions have excellent stability over a pH range of 3 to 9. They do not lose their effectiveness during storage.

Glutaraldehyde, at normal use concentrations, has been reported by some hospital personnel to have a pungent odor and to be irritating to the eyes and nasal passages. Jacobs, U.S. Pat. No. 4,436,754, discloses the use of glycol additives to reduce the odor and irritation properties of glutaraldehyde compositions. Compositions containing phthalaldehyde as the sole active ingredient are odorless and nonirritating to the eyes and nasal passages.

Since equipment turn-around time is very important when considering methods for high level disinfection and sterilization, compositions that do not coagulate blood or fix tissue to equipment are very desirable. In addition, these properties also aid in the disinfection and sterilization process by insuring better surface contact between equipment and the compositions. Glutaraldehyde based compositions tend to coagulate blood and fix tissue to surfaces. Therefore, careful equipment cleaning is a necessary procedure prior to disinfection and sterilization. Phthalaldehyde compositions do not coagulate blood or fix tissue to surfaces. Because of the aforementioned properties and improved efficacy of phthalaldehyde compositions, disinfection and sterilization procedures with these compositions should be faster and more thorough.

SUMMARY OF THE INVENTION

The high level disinfecting compositions of the invertion comprise aqueous solutions having a pH within the range of from 3 to 9, and which have a concentration of phthalaldehyde effective to achieve high level disinfection as determined by the ability of said composition to kill all *Mycobacterium bovis* BCG in crntact with said composition within 10 minutes at 20° C. One method of the invention comprises a method for disinfecting a surface which method comprises immersing said surface in said high level disinfecting composi&ion for a period of time and at a temperature effective &o achieve high level disinfection of said surface.

The sterilizing compositions of the invention comprire aqueous solutions having a pH within the range of frcm 3 to 9, and preferably from 6 to 8, and which have a concentration of phthalaldehyde effective to achieve sterilization as determined by the ability of said composition to kill all spores of *Bacillus subtilis* and *Clostridium sporogenes* in contact with said composition within 24 hours at 20° C. Another method of the invertion comprises a method for sterilizing a surface which comprises immersing said surface in said sterilizing composition for a period of time and at a temperature effective to achieve sterilization of said surface.

DESCRIPTION OF THE INVENTION

Phthalaldehyde has the structure:

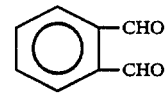

Phthalaldehyde is normally present in the composition, a to use concentration, in amounts of between 0.025% and 1.0% by weight. Higher concentrations, e.g., up to 2%, can be used if desired. The preferred concentration of phthalaldehyde at use dilution is 0.05% to 0.5% by weight. Higher concentrations of phthalaldehyde may be used for shipping the composition to the point of use and the composition can then be diluted with water to the desired use concentration. The limit on the amount of phthalaldehyde used in the concentrate composition is a function of the solubility of phthalaldehyde in water, which is about 5% w/w. To achieve compositions of phthalaldehyde with greater than 5% w/w, a water miscible co-solvent can be used. Suitable co-solvents include methanol, ethanol, isopropanol, glycols, tetrahydrofrran, dimethylsulfoxide and dioxane.

An alkalinating or acidifying salt preferably is used in the compositions of the invention as a buffer to mairtain a desired composition pH during storage and use. The buffer may be of the type disclosed in the Pepper et al. U.S. Pat. No. 3,016,328, which is an alkali metal carbonate or bicarbonate, e.g., sodium bicarbonate or potassium bicarbonate or may be a phosphate. The buffer may also be an organic carboxylate salt such as sodiun citrate, sodium acetate, potassium hydrogen phthalate, potassium citrate, or potassium acetate, or an inorganic borate salt such as potassium or sodium borate. The particular salt or mixture of salts are present in a sufficient amount, 0.05% to 2.5% based on the total weight of the solution, to give the desired pH. The disinfecting properties of the composition are not pH dependent. However, at low phthalaldehyde concentrations (e.g., 0.5% or less) the sporicidal activity of the composition is somewhat pH dependent. The optimal pH range for sporicidal activity is between 6 and 8.

The composition may contain other ingredients such as a surfactant, a corrosion inhibitor, antioxidant, a sequesterent, a dye or a fragrance. The use of these other ingredients is well-known in the art.

The compositions of the invention may be formulated in one or more components. However, if the composition is formulated in two or more parts, the components are combined immediately prior to use.

In carrying out the methods of the invention, the surface of the device to be disinfected or sterilized is immersed in and maintained in contact with the composition of the invention for a period of time and at a temperature effective to achieve disinfection or sterilization. The particular time and temperature chosen can vary, as taught herein, depending on factors such as nature of the device to be sterilized or disinfected (e.g., high temperatures may have to be avoided with certain devices because of heat sensitivity), the pH of the composition, and the like. As a general rule, the following guidelines can be followed in carrying out the methods of the inventior:

To achieve high level disinfection of a surface within 10 minutes at a temperature of 20° C., the pH of the composition can vary within the range of from 3 to 9 and the concentration of the phthalaldehyde should be at least 0.025 percent, based on the weight of the composition. Ordinarily, the concentration of phthalaldehyde will not be greater than about 2 weight percent, although higher concentrations can be used if desired. At higher temperatures, high level disinfection can usually be effected in less than 10 minutes.

To achieve sterilization of a surface within 24 hours at 20° C. with the composition of the invention wherein the composition has a PH within the range of 3 to 9, the concentration of phthalaldehyde should be at least about 0.5 weight percent, based on weight of the composition. At higher concentrations, e.g., at concentrations of at least about 1 weight percent, sterilization can be achieved in as little as 10 hours. When the pH is within the range of from 6 to 8, sterilization can be achieved within 24 hours at 20° C. with a concentration of phthalaldehyde as low as about 0.25 weight percent. The Examples below (particularly Examples VIII and IX) illustrate the sterilization effectiveness of phthalaldehyde at various pH's and concentrations.

In the following Examples, all percentages are weight percentages, based on the total weight of the solutions unless otherwise indicated. In examples showing tuberculocidal test data, the new tuberculocidal test methodology previously described was used.

Example I

In this example, a small amount of phthalaldehyde, and amounts of isophthalaldehyde and terephthalaldehyde at their water solubility limit were tested in aqueous solutions to determine their effectiveness against *Mycobacterium bovis* at 20° C. Use of 20% alcohol cosolvent did not significantly increase the amounts of isophthalaldehyde and terephthalaldehyde in the test solution. The solutions were buffered to pH 8.0 with dipotassium hydrogen phosphate. The results are shown in Table I.

TABLE I

| Aromatic Dialdehyde | % Aromatic Dialdehyde (w/w) | Number of Organisms Surviving | | |
|---|---|---|---|---|
| | | 0 min | 10 min | 20 min |
| Phthalaldehyde | 0.10 | $2.4 \times 10^5$ | 0 | 0 |
| Isophthalaldehyde | 0.25 | $2.8 \times 10^5$ | $2.3 \times 10^5$ | $2\ 3 \times 10^5$ |
| Terephthalaldehyde | 0.10 | $2.8 \times 10^5$ | $3\ 3 \times 10^5$ | $4.0 \times 10^5$ |

The results show that phthalaldehyde, has excellent tuberculocidal activity at low concentration, while isophthalaldehyde and terephthalaldehyde do not have any appreciable tuberculocidal activity.

EXAMPLE II

A series of solutions containing from 0.01 to 0.075% phthalaldehyde, buffered at pH 8 as in Example I, were tested for their effectiveness in killing *Mycobacterium bovis* BCG at 20° C. The results are shown in Table II.

TABLE II

| % Phthalaldehyde (w/w) | Number of Organisms Surviving | | | |
|---|---|---|---|---|
| | 0 min | 2 min | 5 min | 10 min |
| 0.075 | $1.9 \times 10^5$ | $1.2 \times 10^3$ | 0 | 0 |
| 0.05 | $1.9 \times 10^5$ | $5.0 \times 10^3$ | 0 | 0 |
| 0.025 | $1.9 \times 10^5$ | $2.4 \times 10^4$ | $3.2 \times 10^3$ | 0 |

TABLE II-continued

| % Phthalaldehyde (w/w) | Number of Organisms Surviving | | | |
|---|---|---|---|---|
| | 0 min | 2 min | 5 min | 10 min |
| 0.01 | $1.9 \times 10^5$ | $8.0 \times 10^4$ | $4.0 \times 10^4$ | $2.0 \times 10^4$ |

The results indicate that a concentration of only 0.025% phthalaldehyde is tuberculocidal within 10 minutes at 20° C.

EXAMPLE III

Portions of a solution containing 0.1% phthalaldehyde and dipotassium hydrogen phosphate were adjusted to different pH levels with $H_3PO_4$ and KOH. The solutions were tested against *Mycobacterium bovis* BCG at 20° C. to determine the effect of pH on the effectiveness of the solutions. The results are shown in Table III.

TABLE III

| pH | Number of Organisms Surviving | | |
|---|---|---|---|
| | 0 min | 2 min | 5 min |
| 3 | $3.8 \times 10^5$ | $1.4 \times 10^3$ | 0 |
| 5 | $3.8 \times 10^5$ | $5.2 \times 10^2$ | 0 |
| 7 | $3.8 \times 10^5$ | $2.0 \times 10^1$ | 0 |
| 9 | $3.8 \times 10^5$ | $2.0 \times 10^2$ | 0 |

The results indicate that the tuberculocidal activity of phthalaldehyde is not pH dependent.

EXAMPLE IV

Solutions containing 0.1, 0.5, and 1.0% phthalaldehyde buffered to pH 8 with dipotassium hydrogen phosphate were tested to determine the minimum effective concentration required to inactivate a suspension of about $1 \times 10^6$ (6 logs) Poliovirus Type I after 5 minutes exposure to the solutions at 20° C. The results are shown in Table IV.

TABLE IV

| % Phthalaldehyde (w/w) | Reduction in Virus Titer ($\log_{10}$) |
|---|---|
| 0.1 | 3.0 |
| 0.5 | 5.5* |
| 1.0 | 5.5* |

*Total inactivation of virus

The results show that the minimum effective concentration of phthalaldehyde required to totally inactivate Poliovirus Type I in 5 minutes at 20° C. is between 0.1 and 0.5%.

EXAMPLE V

Solutions containing 0.1% phthalaldehyde buffered to pH 7.5 with dipotassium hydrogen phosphate and pH 6 with Potassium acid phthalate were tested against a suspension of about $4.7 \times 10^6$ (6.67 logs) Poliovirus Type I to determine the effect of pH on the reduction of virus titer after 5 minutes exposure to the solutions at 20° C. The results are shown in Table V.

TABLE V

| pH | Reduction in Virus Titer ($\log_{10}$) |
|---|---|
| 6 | 4.2 |
| 7.5 | 4.7 |

The results indicate that the activity of phthalaldehyde against Poliovirus Type I is not significantly dependent on pH over the range of slightly acidic to slightly alkaline.

EXAMPLE VI

A solution containing 0.1% phthalaldehyde buffered to pH 8 with dipotassium hydrogen phosphate was tested to determine its effectiveness in killing *Pseudomonas aeruoinosa* (gram -) and *Staphylococcus aureus* (gram +) at 20° C. using the standard AOAC Use-Dilution Method (AOAC Official Methods of Analysis, 14th edition, 1984, page 67). The results are shown in Table VI.

TABLE VI

| Organism | No. of Positives(Failure)/No. of Total Tests | |
|---|---|---|
| | 5 Min | 10 Min |
| *Pseudomonas aeruoinosa* | 0/30 | 0/30 |
| *Staphylococcus aureus* | 1/30 | 0/30 |

The results show that phthaldehyde is cidal against both gram negative and gram positive bacteria within 10 minutes contact time at 20° C.

EXAMPLE VII

The solution tested in Example VI was tested to determine its effectiveness in killing *Trichophyton mentagrophytes* at 20° C. using the standard AOAC Fungicidal Method (AOAC Official Methods of Analysis, 14th edition, 1984, page 69). The results are shown in Table VII.

TABLE VII

| Test Solution | Growth (+) or No Growth (−) | | |
|---|---|---|---|
| | 5 Min | 10 Min | 15 Min |
| Phthalaldehyde (0.1%) | — | — | — |

The results show that phthalaldehyde is fungicidal in 5 minutes at 20° C.

EXAMPLE VIII

Solutions containing from 0.5% to 2.7% phthalaldehyde were tested to determine the minimum effective concentration required to kill spores of *Bacillus subtilis* and *Clostridium soorooenes* at 20° C. in 10 hours over the pH range 4 to 8 using the standard AOAC Method (AOAC Official Methods of Analysis, 14th edition, 1984, page 72). Solutions at pH 8 were buffered as in Example I and solutions at pH 6 and 4 were buffered with potassium acid Phthalate. The results are shown in Table VIII.

TABLE VIII

| % Phthalaldehyde (w/w) | pH | Total No. of Positives(Failures)/Total No. of Tests | | | |
|---|---|---|---|---|---|
| | | *B. subtilis* | | *C. sporogenes* | |
| | | sutures | penicylinders | sutures | penicylinders |
| 2.7 | 8 | 0/30 | 0/30 | 0/30 | 0/30 |
| 1.0 | 8 | 0/30 | 0/30 | 1/30 | 0/30 |
| 0.5 | 8 | 16/30 | 0/30 | 0/30 | 2/30 |
| 1.0 | 6 | 0/30 | 0/30 | 0/30 | 0/30 |
| 0.5 | 6 | 30/30 | 19/30 | 1/30 | 0/30 |
| 1.5 | 4 | 0/30 | 0/30 | 0/30 | 0/30 |
| 1.0 | 4 | 2/30 | 4/30 | 0/30 | 0/30 |

The results indicate that the minimum effective concentration of phthalaldehyde which is sporicidal at 20° C. in 10 hours is about 1% at pH 8, 6 and 4.

EXAMPLE IX

A series of solutions containing from 0.1 to 1.0% phthalaldehyde was tested to determine the minimum effective concentration required to kill spores of *B. subtilis* and *C. sporogenes* at 20° C. in 24 hours over the pH range 4 to 8. The results are shown in Table IX. Note: *C. sporogenes* was not tested in all cases, since *B. subtilis* was shown to be the more resistant organism in Example VIII.

TABLE VIII

| % Phthalaldehyde (w/w) | pH | Total No. of Positives(Failures)/Total No. of Tests | | | |
|---|---|---|---|---|---|
| | | *B. subtilis* | | *C. sporogenes* | |
| | | sutures | penicylinders | sutures | penicylinders |
| 1.0 | 8 | 0/30 | 0/30 | 0/30 | 0/30 |
| 0.5 | 8 | 0/30 | 0/30 | 0/30 | 0/30 |
| 0.25 | 8 | 0/30 | 0/30 | — | — |
| 0.1 | 8 | 14/30 | 11/30 | — | — |
| 1.0 | 6 | 0/30 | 0/30 | 0/30 | 0/30 |
| 0.5 | 6 | 0/30 | 0/30 | 0/30 | 0/30 |
| 0.25 | 6 | 1/30 | 0/30 | — | — |
| 0.1 | 6 | 30/30 | 30/30 | — | — |
| 1.0 | 4 | 0/30 | 0/30 | 0/30 | 0/30 |
| 0.5 | 4 | 7/30 | 5/30 | 0/30 | 0/30 |
| 0.25 | 4 | 28/30 | 30/30 | — | — |
| 0.1 | 4 | 28/30 | 29/30 | — | — |

The results indicate that the minimum effective concentration of phthalaldehyde which is sporicidal at 20° C. in 24 hours is about 0.25% at both pH 8 and 6 and between 0.5% and 1.0% at pH 4.

EXAMPLE X

Solutions containing 0.3% phthalaldehyde buffered to pH 8 and pH 6 as in Example V were stored at 40° C. for 6 months to determine the effect of pH on the stability of the solutions under accelerated aging conditions. The results are shown in Table X.

TABLE X

| Storage time (months) | pH | % Phthalaldehyde (±0.03%) |
|---|---|---|
| 0 | 8.00 | 0.28 |
| 2 | 7.87 | 0.28 |
| 6 | 7.76 | 0.32 |
| 0 | 6.00 | 0.26 |
| 2 | 5.99 | 0.26 |
| 6 | 6.00 | 0.24 |

The results show that phthalaldehyde solutions have excellent storage stability at both alkaline and acidic pH.

EXAMPLE XI

Glass slides that were stained with 0.05 gram of human blood and dried for 5 minutes at 22° C. to 25° C. were immersed in two solutions containing 0.3% phthalaldehyde. The pH of both phthalaldehyde solutions was adjusted to pH 7.5. The compositions of the phthalaldehyde solutions only differed in the presence or absence of 0.2% nonlonic surfactant. Observations of the blood removal properties for the phthalaldehyde solutions were made after 5 and 15 minutes contact time with the stained slides. The blood removal property of the solutions was graded on the basis of assigning a number from 1 to 7; where 1 signified no removal and 7 complete removal. The results were compared to the blood removal capabilities of a 2% glutaraldehyde solution (pH 7.5) with 0.2% nonionic surfactant. The results are shown in Table XI.

TABLE XI

| Test solutions | Cleaning ratings | |
| --- | --- | --- |
|  | 5 min. contact | 15 min. contact |
| 2% Glutaraldehyde/ 0.2% Surfactant | 1 | 3 |
| 0.3% Phthalaldehyde | 7 | 7 |
| 0.3% Phthalaldehyde/ 0.2% Surfactant | 7 | 7 |

The results show that phthalaldehyde compositions removed 100% of the blood in 5 minutes from the stained slides.

What is claimed is:

1. An odorless high level disinfecting composition comprising an aqueous solution having a pH within the range of from 3 to 9 and which contains an amount of phthalaldehyde effective to achieve high level disinfection as determined by the ability of said composition to kill all *Mycobacterium bovis* BCG in contact with said composition within 10 minutes at 20° C.

2. A method for disinfecting a surface which comprises immersing said surface in and maintaining said surface in contact with the high level disinfecting composition of claim 1 for a period of time and at a temperature effective to achieve high level disinfection of said surface.

3. The method of claim 2 wherein the phthalaldehyde concentration in said high level disinfecting composition is between 0.025 and 2.0 weight percent.

4. The method of claim 2 wherein the phthalaldehyde concentration in said high level disinfecting composition is between 0.025 and 1.0 weight percent.

5. An odorless sterilizing composition comprising an aqueous solution having a pH within the range of from 3 to 9 and which contains an amount of phthalaldehyde effective to achieve sterilization as determined by the ability of said composition to kill all spores of *Bacillus subtilis* and *Clostridium sporogenes* in contact with said composition within 24 hours at 20° C.

6. A method for sterilizing a surface which comprises immersing said surface in and maintaining said surface in contact with the sterilizing composition of claim 5 for a period of time and at a temperature effective to achieve sterilization of said surface.

7. The method of claim 6 wherein the phthalaldehyde concentration in said sterilizing composition is at least 0.5 weight percent.

8. The method of claim 6 wherein the pH of said sterilizing composition is within the range of from 6 to 8 and wherein said phthalaldehyde concentration in said sterilizing composition is at least 0.25 weight percent.

* * * * *